United States Patent [19]
Haydon

[11] Patent Number: 5,180,383
[45] Date of Patent: Jan. 19, 1993

[54] METHOD AND DEVICE FOR ATTACHING ARTIFICIAL JOINT IMPLANTS TO THE ENDS OF BONES

[76] Inventor: Frank A. Haydon, P.O. Box 1295, Franklin, N.C. 28734

[21] Appl. No.: 773,210

[22] Filed: Oct. 9, 1991

[51] Int. Cl.⁵ .............................................. A61F 2/02
[52] U.S. Cl. .................................... 606/72; 606/73; 623/22
[58] Field of Search ........... 606/72, 73, 86, 95; 623/22

[56] References Cited

U.S. PATENT DOCUMENTS

| | | | |
|---|---|---|---|
| 3,641,590 | 2/1972 | Michele | 623/22 |
| 3,740,769 | 6/1973 | Haboush | 623/22 |
| 3,903,549 | 9/1975 | Deyerle | 606/73 X |
| 3,939,497 | 2/1976 | Heimke et al. | 623/22 |
| 4,754,749 | 7/1988 | Tsou | 606/73 |
| 4,944,759 | 9/1989 | Mallory | 623/22 |
| 4,955,325 | 9/1990 | Zarnowski et al. | 623/22 |
| 4,963,152 | 7/1989 | Hofmann | 623/18 |
| 4,963,152 | 10/1990 | Noesherger | 623/20 |
| 4,963,153 | 10/1990 | Kampner | 623/16 |
| 4,990,161 | 2/1991 | Surer | 606/72 X |

Primary Examiner—Robert A. Hafer
Assistant Examiner—Sam Rimell

[57] ABSTRACT

A method and device for attaching with compression artificial joint implants to the ends of bone by means of an independent anchor and dead man (1).

1 Claim, 5 Drawing Sheets

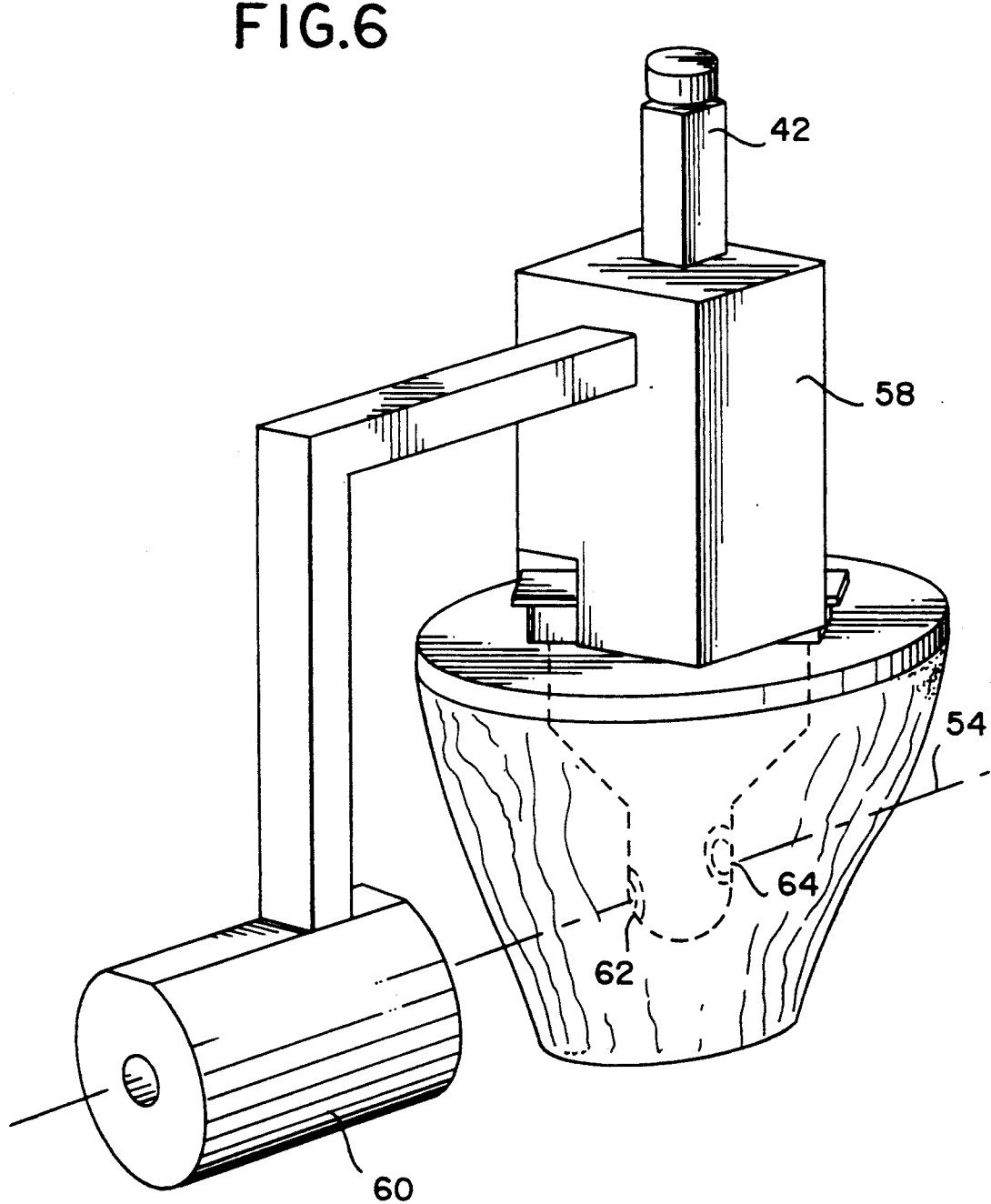

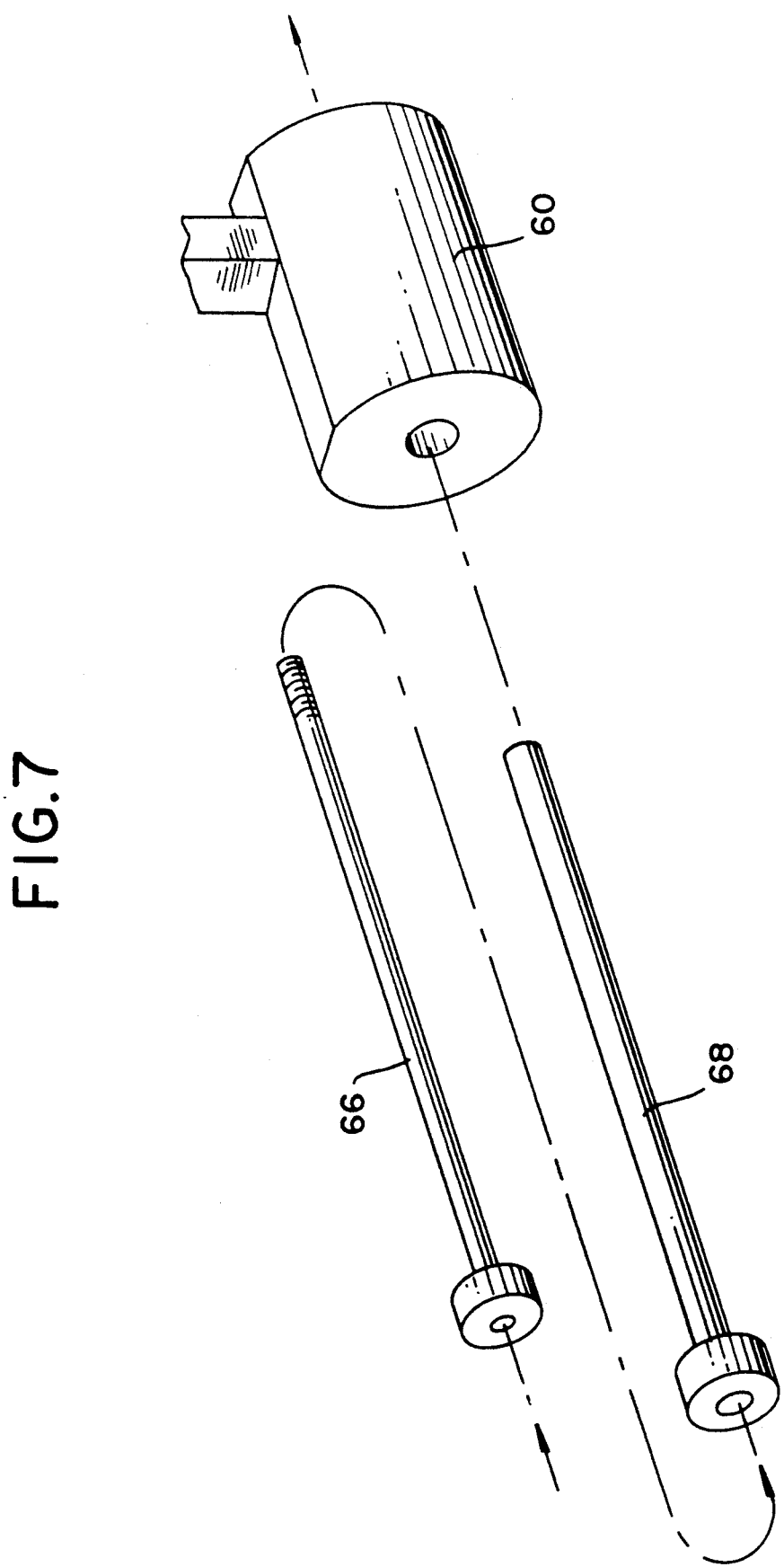

1

METHOD AND DEVICE FOR ATTACHING ARTIFICIAL JOINT IMPLANTS TO THE ENDS OF BONES

BACKGROUND OF THE INVENTION

This system is intended to be used by qualified surgeons in the field of orthopedics in human and veterinary medicine with specific application to artificial joint surgery. The system provides compression fixation of an artificial joint implant to the ends of bone. The current methods used to fix artificial joint implants to bone utilize polymethyl methacrylate bone cement which loosens in time secondary to adjacent tissue reaction of live bone. Poly-methyl methcrylate bone cement has been associated with intraoperative hypotension, allergic reactions, and chemical hepatitis. Another method used to fix artificial joint implants to the ends of bone utilizes intramedullary pegs driven down into the medullary canal of bone. This principle does not provide compression nor does it provide resistance to pull out. Expandable polyethylene pegs have been incorporated into the fixation of artificial joint implants but fail to provide compression and the fixation is dependent upon friction generated between the expandable peg and the friable cancellous bone. Numerous configurations of the artificial joint implant prosthesis base plate have been devised to improve upon fixation but rely primarily upon the strength of the friable cancellous bone. Large cancellous screws placed through the artificial joint implant have been employed but again are limited in their ability to secure the artificial joint implant based upon the limited resistance to pull-out offered by cancellous bone. The anchoring system describe herein provides compression which exceeds that which can be achieved by any current method of fixation. By improving fixation of the artificial joint implant to the ends of bone, facilitate bone ingrowth for physiologic bonding and provides improved resistance against physiologic forces applied across the joint.

OBJECTIVES AND ADVANTAGES

The objectives and advantages are achieved by recessing an anchoring device below the level of the osteotomy for the artificial joint implant and securing the anchor to cortical bone by means of a dead man. Once the anchor has been fastened, a metal-backed artificial joint implant can be placed on top of the osteotomy site and secured to the achoring device by means of machine bolts to apply compressive forces. Since the anchor is secured to cortical bone by a dead man, the compressive forces resisting pull-out are determined by the strength of the cortical bone which far exceeds the forces resisting pull-out from cancellous bone.

DESCRIPTION OF THE DRAWINGS

FIG. 6 represents a perspective view of an index guide sitting on top of the anchor handle assembly in a coronal plane.

FIG. 7 represents an exploded view of a drill cannula, screw cannula fitting through an index drill guide cannula.

DESCRIPTION OF HOW THE SYSTEM WORKS

Figures 1, 2, 3:
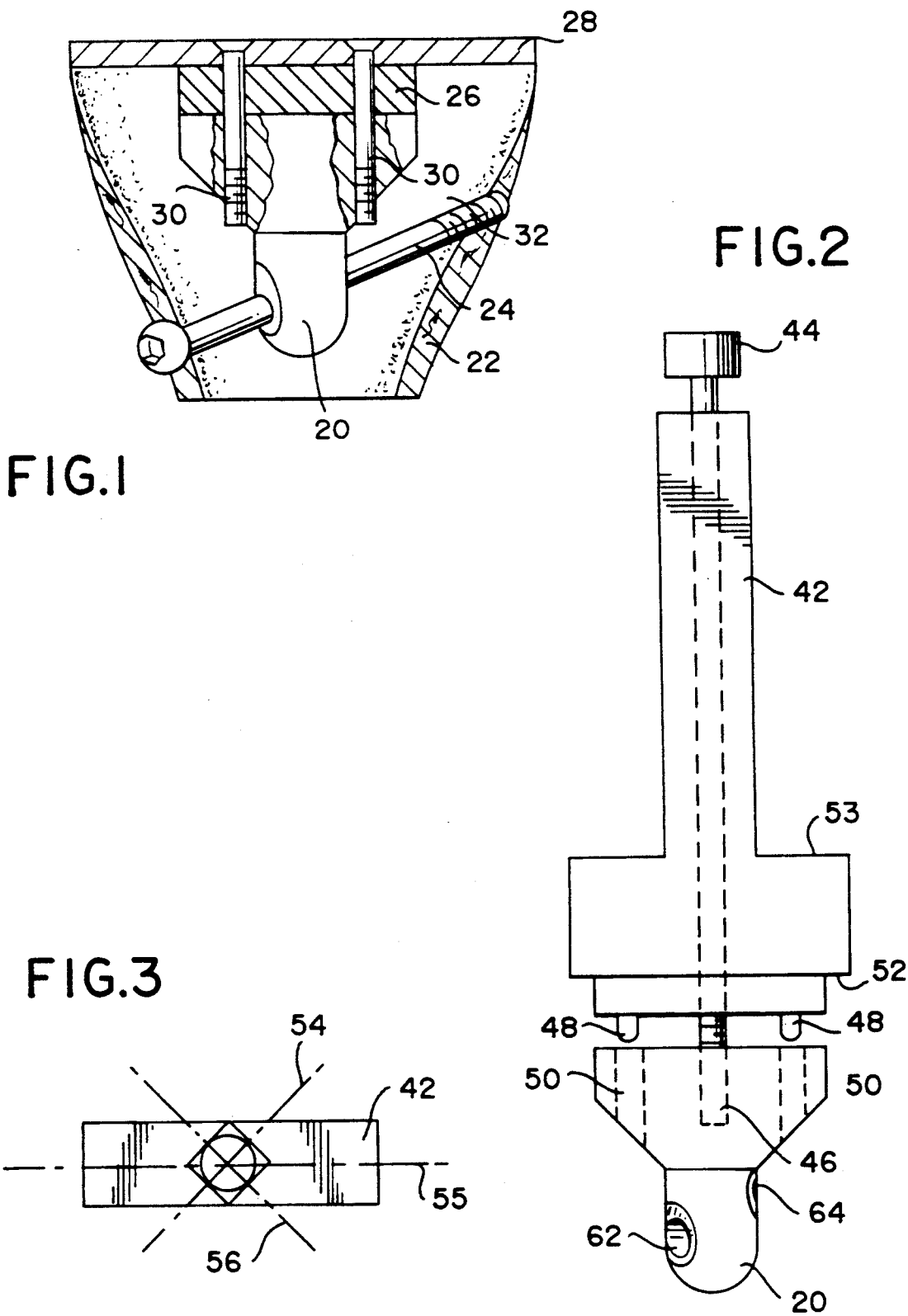
FIG. 1 shows a coronal section through a bone with an artificial joint implant secured to an anchor with a dead man bolt fastened to cortical bone.
FIG. 2 represents an exploded perspective view of an anchor handle and its attachment to the anchor.
FIG. 3 shows the anchor handle viewed from top demonstrating two indexable axes for a drill guide.

FIG. 1 shows an implant anchor 20 fastened to cortical bone 22 by dead man 24. The anchor is recessed 26 below an artificial joint implant 28 and fastened to the anchor by machine bolts 30.

Figure 5:
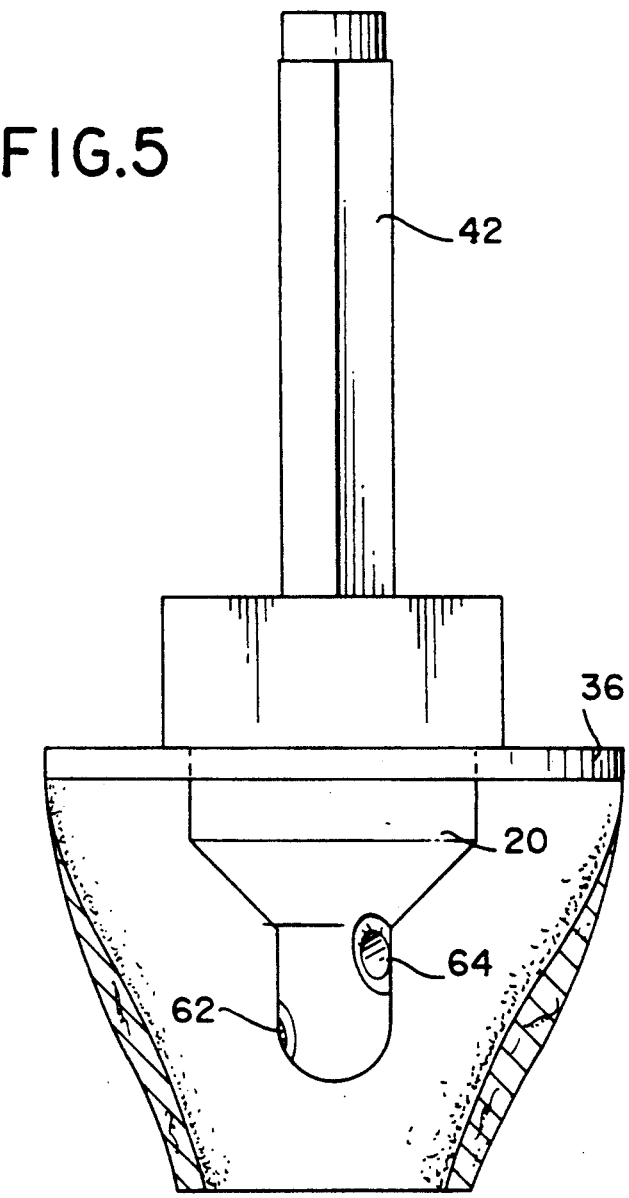
FIG. 5 shows a coronal section of the anchor handle anchor assembly placed through the template in a bone.
Figure 4:
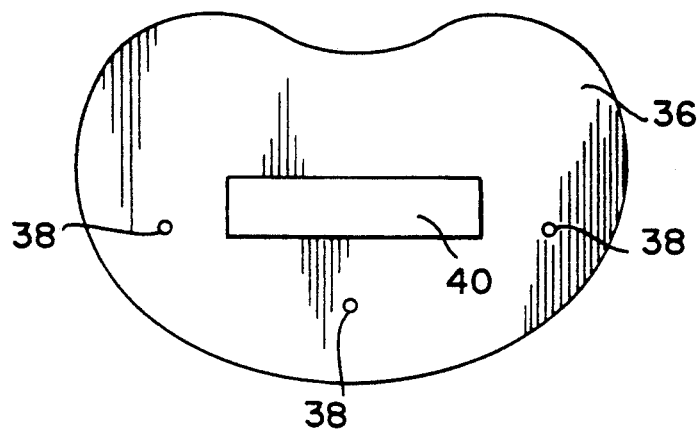
FIG. 4 represents a top view of a template.
Figure 9:
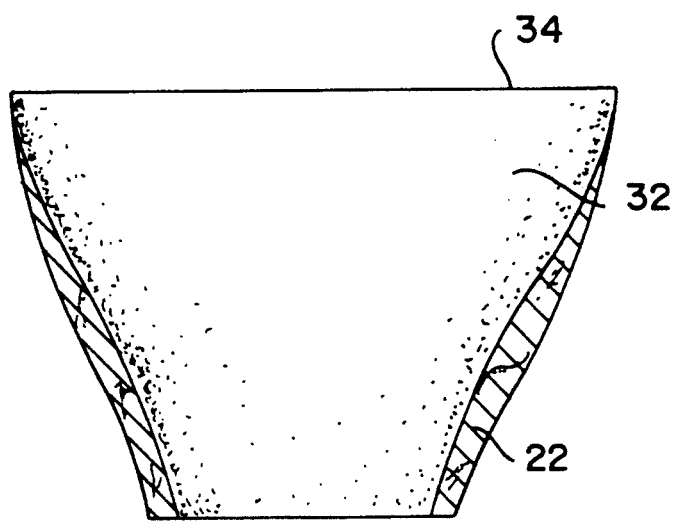
FIG. 9 is a coronal section through a typical tubular or appendicular bone.

FIG. 9 represents a cross-section of a typical prepared surface of bone ready to receive an artificial joint implant. A hard cortical bone 22 encases soft cancellous bone 32 with a transverse cut surface 34. A template FIG. 4, No. 36 is matched and sized to the transverse bone surface FIG. 9, No. 34 and secured with pins through pin holes 38 to provide temporary fixation. An anchor hole in the template FIG. 4, No. 40, is used to position the anchor. FIG. 2 shows the anchor 20 secured to an anchor handle 42 by an anchor handle bolt 44 which threads into an anchor handle bolt hole 46. Guide pegs 48 align the anchor handle to the anchor by fitting into threaded machine bolt holes 50. FIG. 5 shows the anchor handle and anchor assembly passed through the anchor hole in the template so that Ledge 1, FIG. 2, No. 52 sits on top of the template FIG. 4, No. 36.

FIG. 3 shows the anchor handle from top projection to be a square configuration oriented so that the diagonal through the handle is parallel to the coronal plane. This provides two indexable axes FIG. 3, No. 54 and 56, for alignment of a drill guide, FIG. 6, No. 58. The indexable drill guide, FIG. 6 No. 58, fits over the anchor handle and sits on Ledge 2, No. 53. This can orient along two axes perpendicular to one another. In FIG. 6 the index drill guide is aligned along Axis 54 so that a cannular guide aligns with the appropriate dead man hole, FIG. 2, No. 62.

Figure 8:
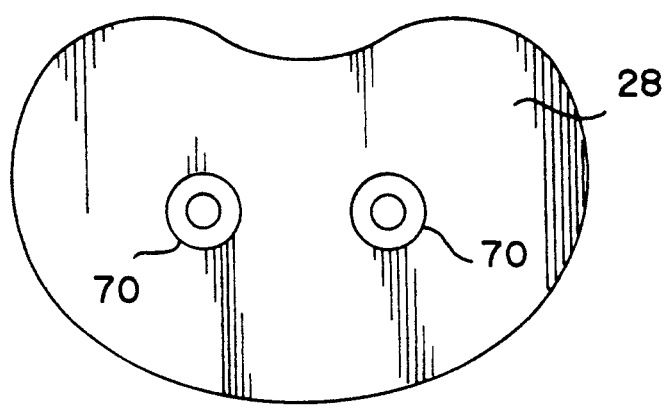
FIG. 8 is a top view of an artificial joint implant adapted for use with the anchor.

FIG. 7 shows a concentric drill cannula 66 fitting into a screw cannula 68 fitting into the cannula guide 60. The cannulas are advanced towards bone through the cannula guide. A drill is passed through the drill guide near cortex of bone, dead man hole, far cortex of bone and removed. The drill cannula is removed leaving the screw cannula in place. A large diameter drill matching the diameter of the dead man hole is passed through the near cortex of bone. The large drill bit is removed. A self tapping dead man screw is placed through the screw cannula into the bone as demonstrated in FIG. 1. The index guide, anchor handle, and template are removed. An artificial joint implant FIG. 8 is then fastened to the anchor with machine bolts producing compression between the end of the bone and the artificial joint implant.

CONCLUSION

The method presented can be adapted to the ends of all tubular bones in the appendicular skeleton. Compression can be applied to all metal back prostheses by minor modification of providing holes for the machine bolts FIG. 8, No. 70. This system can be used to fasten artificial joint implants to the ends of all tubular bone.

This system would be feasible for securing the femoral component in the artificial knee implant, the femoral component in the artificial hip implant, the humeral component in the artificial shoulder joint implant, the humeral component in the artificial elbow implant, the ulnar component in the artificial elbow implant, the radial component in the artificial wrist implants, the tibial component in the artificial ankle joints, the proximal and distal ends of the metatarsals and metacarpals, and the proximal and distal ends of the phalanges.

I claim:

1. An apparatus for retaining a joint implant comprising:

an anchor implantable within a bone, said anchor defining a longitudinal axis and having a lower proximal end and upper distal end, the upper distal end being widened relative to the lower proximal end and defining at least two, spaced, threaded apertures, the lower proximal end defining a single aperture, with said single aperture being angled with respect to said longitudinal axis;

two threaded countersunk bolts connectably engaging two of said apertures in said anchor and extending above the edge of said bone for retaining the implant on the bone edge;

a dead man bolt having a head portion and a threaded portion, said dead man bolt extending through said single angled aperture so that said head and threaded portion of the dead man bolt engage outer cortical portions of the bone and retain the anchor within the bone.

* * * * *